United States Patent [19]
Krause et al.

[11] Patent Number: 5,874,422
[45] Date of Patent: Feb. 23, 1999

[54] USE OF NON-STEROIDAL ANTI-INFLAMMATORY AGENTS TO IMPROVE THE PHYSIOLOGICAL COMPATIBILITY OF PARTICULATE PHARMACEUTICAL PREPARATIONS

[75] Inventors: Werner Krause, Berlin; Peter Muschick, Ladeburg, both of Germany

[73] Assignee: Schering Aktiengesellschaft, Germany

[21] Appl. No.: 945,857

[22] PCT Filed: May 9, 1996

[86] PCT No.: PCT/EP96/01936

§ 371 Date: Jan. 27, 1998

§ 102(e) Date: Jan. 27, 1998

[87] PCT Pub. No.: WO96/35429

PCT Pub. Date: Nov. 14, 1996

[30] Foreign Application Priority Data

May 10, 1995 [DE] Germany ................ 195 18 221.9

[51] Int. Cl.⁶ ............................ A61K 31/60; A61K 31/19
[52] U.S. Cl. ............................................. 514/165; 514/570
[58] Field of Search ..................................... 514/165, 570

[56] References Cited

FOREIGN PATENT DOCUMENTS

WO 88/09165   12/1988   WIPO .

OTHER PUBLICATIONS

Cancer Immunol. Immunother. vol. 36, No. 1 pp. 45–51, 1993.

*Primary Examiner*—Raymond Henley, III
*Attorney, Agent, or Firm*—Miller, White, Zelano, & Branigan, P.C.

[57] ABSTRACT

The use of nonsteroidal anti-inflammatory agents as an addition to particulate pharmaceutical agent preparations can reduce side-effects on the cardiovascular system during administration.

9 Claims, 4 Drawing Sheets

USE OF NON-STEROIDAL ANTI-INFLAMMATORY AGENTS TO IMPROVE THE PHYSIOLOGICAL COMPATIBILITY OF PARTICULATE PHARMACEUTICAL PREPARATIONS

This is a 371 of PCT/EP96/01936 filed May 9, 1996.

SUBJECT OF THE INVENTION

The invention relates to the subjects that are characterized in the claims, i.e., the use of nonsteroidal anti-inflammatory agents to improve the physiological compatibility of particulate pharmaceutical agent preparations.

PRIOR ART

Particulate pharmaceutical preparations, such as, e.g., liposomes, magnetites, cavisomes, nanoparticles, etc., have in recent years gained increasing importance in both diagnosis and therapy. Some of these particulate systems, especially liposomes and cavisomes, can in turn be suitable as vehicle systems for transporting diagnostically significant compounds, such as, e.g., contrast media or therapeutically usable substances, such as, e.g., gentamicin (INN). (Seltzer, S.: Liposomes in Diagnostic Imaging, in: Gregoriadis, G. (ed.), Liposomes as Drug Carriers, J. Wiley & Sons, Ltd., Chichester, New York, Brisbane, Toronto, Singapore, 1988).

After intravenous administration, such particulate vehicle systems are concentrated preferably in the organs of the mononuclear phagocyte system (RES), whereby the highest concentrations were reached in the liver and spleen (Krause, W. et al., J. Liposome Research 1995; 5:1–26).

WO88/09165 describes injectable aqueous liposome preparations with iodine-containing x-ray contrast media, as well as a process for the production of corresponding formulations. Owing to the sizes (0.15–0.3 $\mu$m), as well as the high contrast medium inclusions (iodine/lipid quotient 1.5–6), these formulations are especially suitable for visualizing the liver.

Very high dosages, which may very well be in the order of magnitude of 10 g of lipid and more, are necessary especially for the particulate formulations that are used in diagnosis, and here again mainly for the preparations that are used in diagnostic radiology (standard x-ray, but also computer tomography). The result is strong activation of the reticuloendothelial system (RES) and other defense mechanisms. This can result in, i.a., the reactions described below: a drop in the mean and arterial blood pressure and peripheral resistance, and an increase in heart rate, contractility, cardiac output, and pressure in the pulmonary circulation.

Waddel et al. (J. Lab. Clin. Med. 1955; 45:697–710) describe these side-effects in patients after injection of lipid emulsions as follows: reddening of the skin, sensation of warmth in the face and on the neck, agitation, sensation of stenosis or pressure in the chest area, cyanosis, and strong back pains. The administration of antihistamines is not able to eliminate or mitigate these side-effects.

Behan et al. (AJR 1993; 160:399–405) observed a similar side-effect spectrum after an emulsion of perfluorooctylbromide was infused. Although it was possible to alleviate these effects with hydrocortisone, this compound is not used for computer tomography because of the high risk of side-effects. Similar results were described by Vercelloti et al. (Blood 1982; 59:1299–1304).

Rabinovici et al. (Circ. Shock 1990; 31:431–445) speculate that the undesirable effects of liposomes with encapsulated hemoglobin are attributable to the release of PAF (platelet-activating factor), and they attempted—successfully—to inhibit them by administering a PAF antagonist.

After administration of diatrizoate-containing liposomes to patients with Hodgkins lymphoma, cirrhosis of the liver, or liver tumors, Rosenberg et al. (Vestn. Rontgenol. Radiol. 5:35–8, 1993) describe side-effects such as elevated temperature and fever in 30% of the patients. It was possible to reduce or eliminate these effects by pretreatment with prednisolone (INN) and pipolphen.

It has now been found, surprisingly enough, that a direct addition of nonsteroidal anti-inflammatory agents to particulate formulations not only can reduce the undesirable effects on the cardiovascular system, but can even completely prevent them.

This is especially surprising because the side-effects without addition of nonsteroidal anti-inflammatory agents begin immediately after the start of the administration (see FIG. 1). The elimination of side-effects by nonsteroidal anti-inflammatory agents is therefore effective even at the low starting concentration of these substances in the blood stream that is present at the beginning of the administration.

DESCRIPTION OF THE SUBJECT OF THE INVENTION

The subject of this invention is the use of nonsteroidal anti-inflammatory agents to improve the physiological compatibility of particulate pharmaceutical preparations.

As particulate pharmaceutical preparations, magnetites, nanoparticles, cavisomes, or liposomes, especially liposomes, which contain x-ray or NMR contrast media, can be used. Particles that are used as vehicles for diagnostic agents or therapeutic agents are also suitable, however. The corresponding preparation can always be administered at the dose that is commonly used and that contains the commonly used galenic additives.

As nonsteroidal anti-inflammatory agents, for example, acetylsalicylic acid, indomethacin (INN), ibuprofen (INN) or ketoprofen (INN), especially acetylsalicylic acid, can be used. The anti-inflammatory agents can be contained in the pharmaceutical agent at the commonly used dose, e.g.: acetylsalicylic acid at a dose of 0.1–50 mg/kg of body weight, preferably 5–15 mg/kg of body weight.

Such pharmaceutical preparations and agents are therefore also the subject of the invention.

Figure 1:
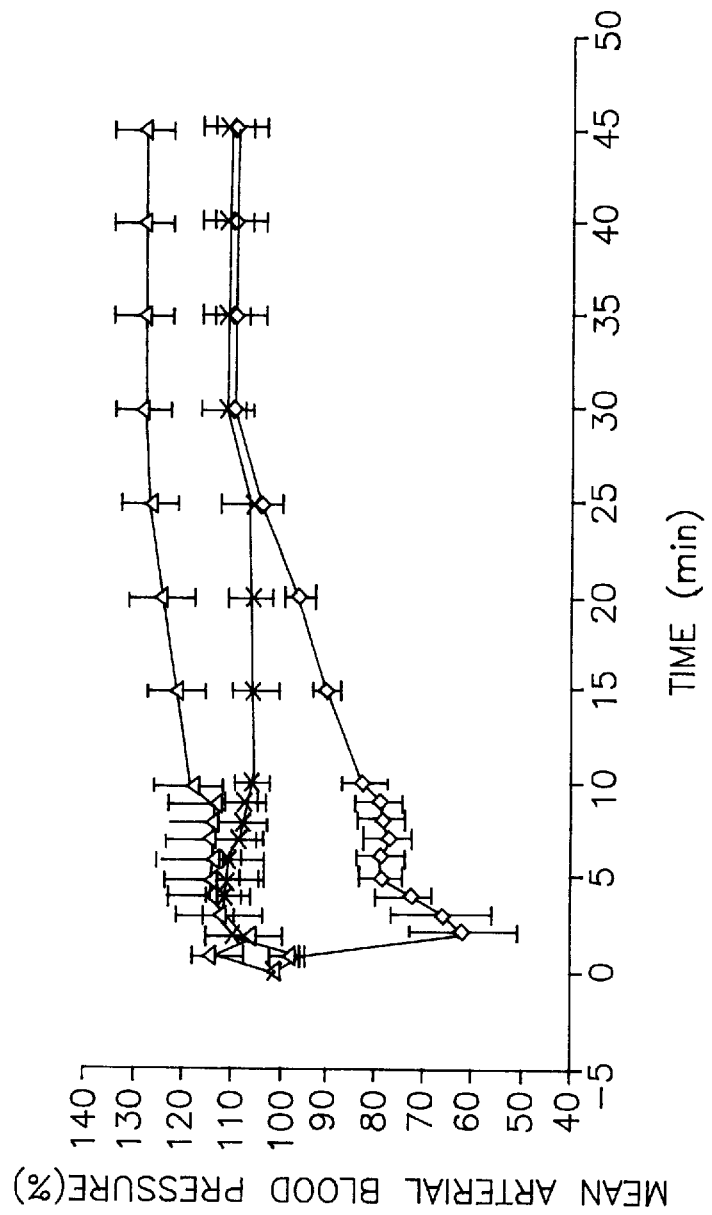
FIG. 1 Is a graph of mean arterial blood pressure in rats versus time (N=6; mean value ±SEM) after injection of liposomes without acetylsalicylic acid ($\Diamond$), of liposomes with acetylsalicylic acid ($\Delta$) and of a mannitol solution with acetylsalicylic acid (x).

after injection of liposomes (250 mg of iodine/kg) with acetylsalicylic acid premedication (♦) in comparison with the control (Ultravist) (□).

The following examples are intended to explain the invention, without intending that they have a limiting effect.

EXAMPLE 1

Male Wistar rats (350 g, N=6) were anesthetized with pentobarbital-Na (60 mg/kg i.p.) and then received an intravenous injection of liposomes that were charged with the x-ray contrast medium iopromide (INN). The particle diameter of the liposomes was about 0.5 μm, and the composition consisted of soy phosphatidylcholine/cholesterol/stearic acid (4:5:1, suspension in mannitol solution). The dose was 300 mg of iodine/kg, and the rate of injection 100 mg of iodine/kg/minute. As a control, a mannitol solution (300 mmol, identical volume) was examined in N=4 animals. In another group of N=6 rats, acetylsalicylic acid solution (Aspisol®; 4 mg/ml) was added to the liposome suspension by mixing in the syringe.

Unlike in the mannitol control, the administration of the liposome formulation resulted in a strong reduction in mean blood pressure (to 60% of the starting value). With the addition of acetylsalicylic acid, the hemodynamic side-effects that are normally to be observed from the liposomes were completely prevented.

The results are depicted in FIG. 1.

EXAMPLE 2

After premedication, male German land race pigs (40 kg, N=6) were intubated with azaperone/ketamines (1.5/10 mg/kg) and supplied with air with a mixture of nitrous oxide/oxygen (3:1) and 1% by volume of enfluane. After muscle relaxation with 0.1 mg/kg of pancuronium bromide, the right jugular vein and the right carotid artery were cannulated. A tip manometer was pushed via the jugular vein through the right cardiac ventricle into the pulmonary artery to measure pressure (PAP). A double-sensor tip manometer was implanted via the carotid artery to measure blood pressure (BP) and the pressure in the left cardiac ventricle (LVP). The electrocardiogram (EKG), the heart rate (HR), and the pressure increase or drop rate (dP/dtmax and min) were also recorded continuously. In addition, after medisternal thoracotomy, cardiac output relating to the right ventricle (SV) and cardiac output (CO) were measured.

Then, after a suitable adaptation period, the animals received an infusion of liposomes that were charged with an x-ray contrast medium. The particle diameter was about 0.2 μm, and the composition consisted of soy phosphatidylcholine/cholesterol/soy phosphatidyl glycerol (6:3:1). The dose was 10 or 250 mg of iodine/kg, and the rate of injection was 10 mg of iodine/kg/minute. In pigs the administration of the liposome formulation (10 mg of iodine/kg) led to an increase in PAP and a decrease in CO.

Figure 2:
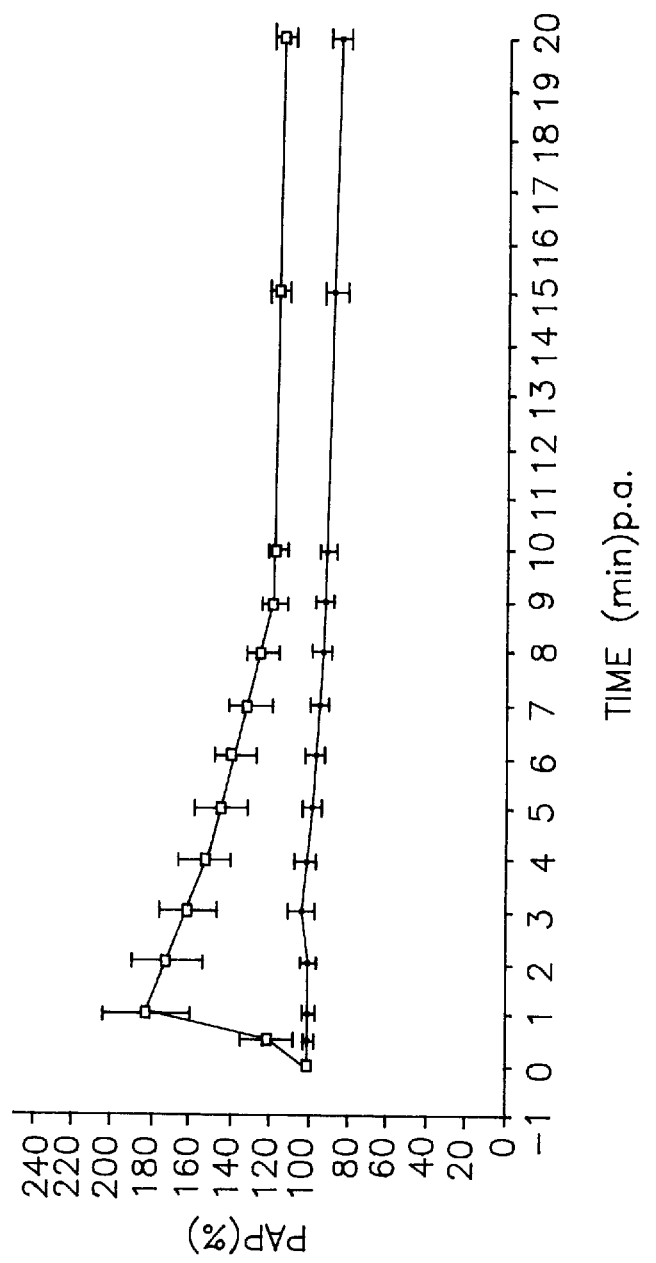
FIG. 2 Is a graph of plumonary arterial pressure (PAP) in German land race pigs versus time (N=6; mean value±SEM) after injection of liposomes (10 mg of iodine/kg) without acetylsalicylic acid premedication ($\square$) or with acetylsalicylic acid premedication ($\blacklozenge$).
Figure 3:
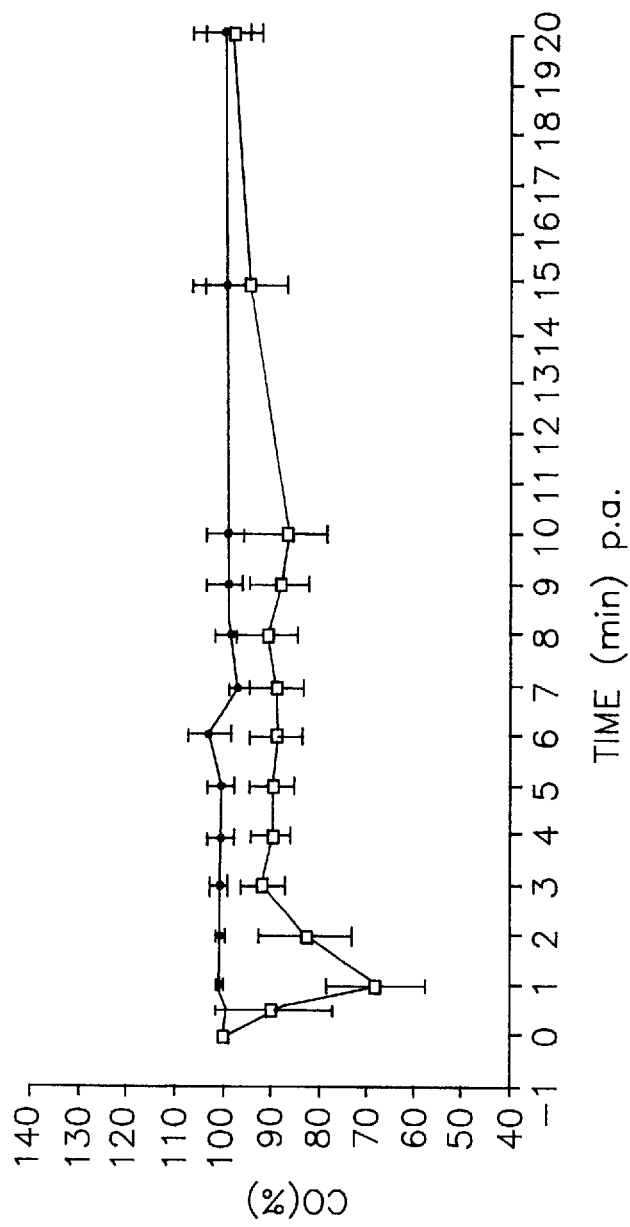
FIG. 3 Is a graph of cardiac output of the right ventricle in German land race pigs verses time (N=6; mean value±SEM) after injection of liposomes (10 mg. of iodine/Kg) without acetylsalicylic acid premedication ($\square$) or with acetylsalicylic acid premedication ($\blacklozenge$).
Figure 4:
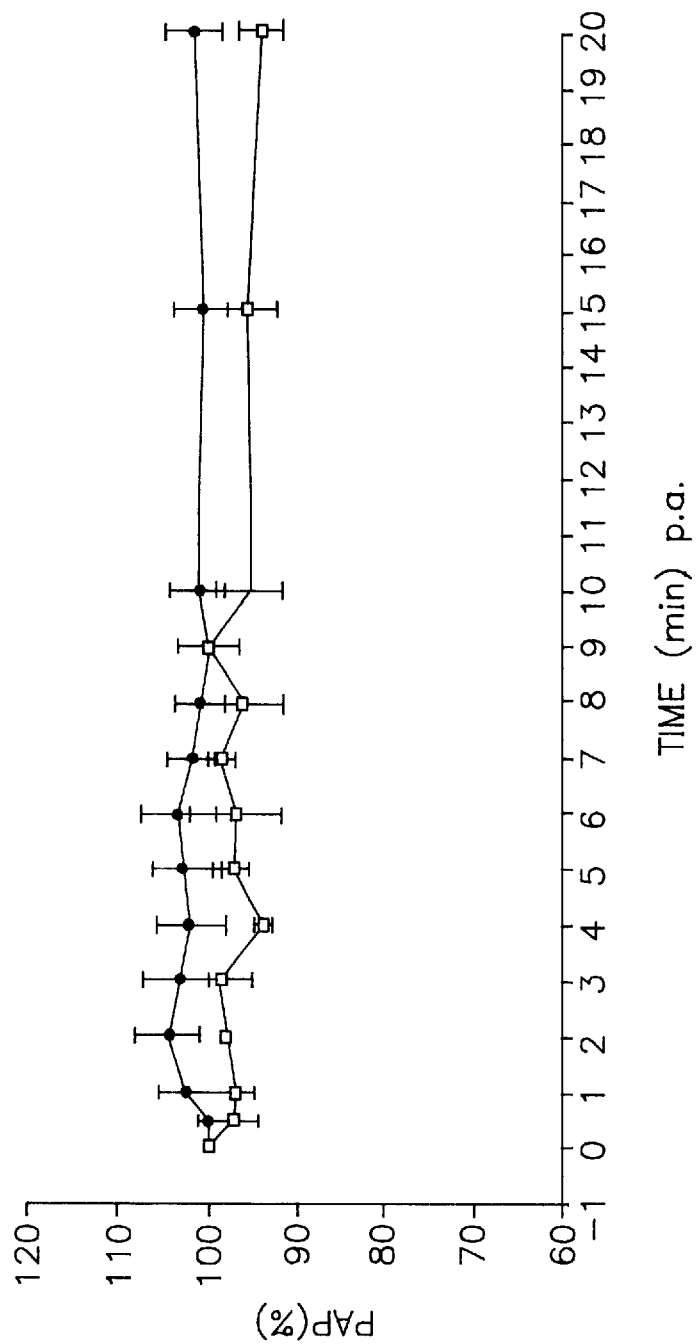
FIG. 4: Is a graph of pulmonary arterial pressure PAP in German land race pigs verses time (N=3; mean value±SEM)

By premedication with acetylsalicylic acid (ASA, 10 mg/kg), it was possible to completely prevent these circulatory side-effects (FIG. 2 and 3). By premedication with ASA (10 mg/kg) 5 minutes before the liposome infusion, it was also possible to completely prevent all side-effects at a liposome dose of 250 mg/kg (FIG. 4).

We claim:

1. A method of using non-steroidal anti-inflammatory agents which comprises incorporating a non-steroidal anti-inflammatory agent into a particulate pharmaceutical preparation in an amount sufficient to improve the physiological compatibility of said particulate pharmaceutical preparation.

2. A method as in claim 1 wherein the non-steroidal anti-inflammatory agent is selected from the group consisting of acetylsalicylic acid, indomethacin (INN), ibuprofen (INN), and ketoprofen (INN).

3. A method of using non-steroidal anti-inflammatory agents which comprises adding a non-steroidal anti-inflammatory agent to magnetites, nanoparticles, cavisomes, liposomes, or particulate vehicle systems.

4. A method of using non-steroidal anti-inflammatory agents which comprises adding a non-steroidal anti-inflammatory agent to liposomes that contain contrast media.

5. A method of using non-steroidal anti-inflammatory agents which comprises adding a non-steroidal anti-inflammatory agent to particulate vehicle systems that contain diagnostic agents and/or therapeutic agents.

6. Pharmaceutical preparation that contains at least one x-ray and/or NMR contrast medium in combination with at least one nonsteroidal anti-inflammatory agent.

7. Pharmaceutical preparation according to claim 6 that contains at least one x-ray and/or NMR contrast medium that is encapsulated in liposomes in combination with at least one nonsteroidal anti-inflammatory agent.

8. Pharmaceutical preparation according to claim 6 that contains acetylsalicylic acid.

9. Pharmaceutical preparation according to claim 7 that contains acetylsalicylic acid.

* * * * *